United States Patent [19]
Matsuo et al.

[11] Patent Number: 6,034,234
[45] Date of Patent: Mar. 7, 2000

[54] DOUBLE-STRANDED OLIGONUCLEOTIDE AND ANTICANCER AGENT CONTAINING THE SAME AS ACTIVE INGREDIENT

[75] Inventors: Ken-ichi Matsuo; Yoshikazu Sugimoto; Kenji Suzuki; Keisuke Ishida; Yuji Yamada, all of Saitama, Japan

[73] Assignee: Taiho Pharmaceutical Co., Ltd., Tokyo, Japan

[21] Appl. No.: 08/676,241

[22] PCT Filed: Nov. 16, 1995

[86] PCT No.: PCT/JP95/02348

§ 371 Date: Jul. 17, 1996

§ 102(e) Date: Jul. 17, 1996

[87] PCT Pub. No.: WO96/16074

PCT Pub. Date: May 30, 1996

[30] Foreign Application Priority Data

Nov. 17, 1994 [JP] Japan .................................. 6-283065

[51] Int. Cl.⁷ .................................................. C07H 21/04
[52] U.S. Cl. ...................... 536/24.5; 536/23.1; 536/24.1; 514/44
[58] Field of Search ..................... 514/44; 435/6, 435/7.23, 325; 536/23.1, 24.5, 24.1; 935/33, 34, 76, 77, 78

[56] References Cited

U.S. PATENT DOCUMENTS

| | | | |
|---|---|---|---|
| 5,473,056 | 12/1995 | Ivey-Hoyle et al. | 530/358 |
| 5,496,831 | 3/1996 | Alexander-Bridges et al. | 514/290 |
| 5,563,036 | 10/1996 | Peterson et al. | 435/6 |
| 5,585,479 | 12/1996 | Hoke et al. | 536/24.5 |
| 5,683,985 | 11/1997 | Chu et al. | 514/44 |
| 5,759,803 | 6/1998 | Kaelin, Jr. et al. | 435/69.1 |
| 5,859,226 | 1/1999 | Hunt et al. | 536/24.1 |

FOREIGN PATENT DOCUMENTS

| | | |
|---|---|---|
| WO 93/12225 | 6/1993 | WIPO . |
| WO 95/11687 | 5/1995 | WIPO . |
| WO 95/24223 | 9/1995 | WIPO . |

OTHER PUBLICATIONS

Wagner (Nature. 1994, vol. 372:333–335).
Plenat (J. Mol. Med. Today. 1996, vol.2, No.6:250–257).
Mastrangelo et al. (Seminars in Oncology, vol. 23, 2:4–21 1996).

*Primary Examiner*—Scott D. Priebe
*Assistant Examiner*—Dave Trong Nguyen
*Attorney, Agent, or Firm*—Sughrue, Mion, Zinn, Macpeak & Seas, PLLC

[57] ABSTRACT

This invention provides a double-stranded oligonucleotide or a derivative thereof which comprises 15 to 40 base pairs, wherein at least one side of the strands contains at least one nucleotide sequence represented by 5'-TTTSSCGS-3' (S is G or C). Also, since the compound of the present invention can inhibit expression of growth-related genes which are regulated by E2F, through its function to undergo sequence-specific competitive inhibition of the binding of E2F protein to the transcription region at a low concentration, a pharmaceutical composition containing the inventive compound as its active ingredient is useful as a drug having low side effects for use in the prevention and treatment of cancers.

5 Claims, 5 Drawing Sheets

1   Dumbbell type − Mung bean nuclease

2   Dumbbell type + Mung bean nuclease

1. Control
2. Lipofectin
3. Dumbbell type 10 nM
4. Dumbbell type 30 nM
5. Dumbbell type 100 nM
6. Control
7. Lipofectin
8. Sequence Id No.1  1 nM
9. Sequence Id No.1  3 nM
10. Sequence Id No.1 10 nM Sequence ID No. 1 | Dumbbell type 1 Control
2 + Non-labeled Sequence ID No. 1
3 + Non-labeled Sequence ID No. 4

1 Control
2 + Non-labeled Sequence ID No. 3
3 + Non-labeled Sequence ID No. 4

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 24 base pairs
         (B) TYPE: nucleic acid
         (C) STRANDEDNESS: double
         (D) TOPOLOGY: both (ii) MOLECULE TYPE: other nucleic acid
         (A) DESCRIPTION: /desc = "Synthetic oligonucleotide"

(xi) SEQUENCE DESCRIPTION: SEQ ID NO:1:

TTTGGCGCTT TCGCGCTTTC CCGC                                          24

(2) INFORMATION FOR SEQ ID NO:2:

(i) SEQUENCE CHARACTERISTICS:
         (A) LENGTH: 30 base pairs
         (B) TYPE: nucleic acid
         (C) STRANDEDNESS: double
         (D) TOPOLOGY: both (ii) MOLECULE TYPE: other nucleic acid
         (A) DESCRIPTION: /desc = "Synthetic oligonucleotide"

(xi) SEQUENCE DESCRIPTION: SEQ ID NO:2:

CGGCCACAAT TTCGCGCCAA ACTTGACCGC                                    30

(2) INFORMATION FOR SEQ ID NO:3:

(i) SEQUENCE CHARACTERISTICS:
         (A) LENGTH: 28 base pairs
         (B) TYPE: nucleic acid
         (C) STRANDEDNESS: double
         (D) TOPOLOGY: both (ii) MOLECULE TYPE: other nucleic acid
         (A) DESCRIPTION: /desc = "Synthetic oligonucleotide"

(xi) SEQUENCE DESCRIPTION: SEQ ID NO:3:

GCTTTCCCGC CAAATTTCGC GCGAAAGC                                      28

(2) INFORMATION FOR SEQ ID NO:4:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "Synthetic oligonucleotide"

(xi) SEQUENCE DESCRIPTION: SEQ ID NO:4:

GGTGTCTCGG TCTCTCCGTC TCTC                                          24

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Synthetic oligonucleotide"

(xi) SEQUENCE DESCRIPTION: SEQ ID NO:5:

AAGGCCATGA CGCTCACGGC                                                        20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Synthetic oligonucleotide"

(xi) SEQUENCE DESCRIPTION: SEQ ID NO:6:

GAGCACGACT GACTCCGAGC                                                        20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Synthetic oligonucleotide"

(xi) SEQUENCE DESCRIPTION: SEQ ID NO:7:

AAGCTAACGT TGAGGGGCAT                                                        20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Synthetic oligonuleotide"

(xi) SEQUENCE DESCRIPTION: SEQ ID NO:8:

ATGCCCCTCA ACGTTAGCTT                                                        20

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "Oligonucleotide"

(xi) SEQUENCE DESCRIPTION: SEQ ID NO:9:

TTTSSCGSSA AA                                                                12

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: double

```
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:10:

SCGSSAAATT TSSCGS                                                       16

(2) INFORMATION FOR SEQ ID NO:11:

(i) SEQUENCE CHARACTERISTICS:
            (A) LENGTH: 10 base pairs
            (B) TYPE: nucleic acid
            (C) STRANDEDNESS: double
            (D) TOPOLOGY: both (ii) MOLECULE TYPE: other nucleic acid
            (A) DESCRIPTION: /desc = "Oligonucleotide"

(ix) FEATURE:
            (A) NAME/KEY: misc_feature
            (B) LOCATION: 1
            (D) OTHER INFORMATION: /note= "N is A, T, G or C
                through the linkage of a total of 7 to 32 optional base N
                to its 5'-end."

(ix) FEATURE:
            (A) NAME/KEY: misc_feature
            (B) LOCATION: 10
            (D) OTHER INFORMATION: /note= "N is A, T, G or C
                through the linkage of a total of 7 to 32 optional base N
                to its 3'-end."

(xi) SEQUENCE DESCRIPTION: SEQ ID NO:11:

NTTTSSCGSN                                                              10
```

DOUBLE-STRANDED OLIGONUCLEOTIDE AND ANTICANCER AGENT CONTAINING THE SAME AS ACTIVE INGREDIENT

This application is the U.S. national phase of PCT application PCT/JP95/02348 filed Nov. 16, 1995 with a claim to the priority of Japanese application JP 6/283065 filed Nov. 17, 1994.

TECHNICAL FIELD

This invention relates to a double-stranded oligonucleotide or a derivative thereof which is useful in treating and preventing human cancers.

BACKGROUND ART

With the discovery of a number of cancer-related genes in recent years, revelation of the mechanism of malignant transformation has been started gradually. As the results, it has been shown that many cancers are certain genetic diseases caused by the abnormality of genes. Since abnormal mutant cells are originated from normal cells by nature, they are not easily be recognized as foreign bodies in the living body and differences in their biological or biochemical properties are not so large unlike the case of infectious diseases caused by the invasion of other organisms.

In consequence, though various anticancer drugs, therapeutic methods and reagents have been developed, they exert influences upon not only cancer cells but also normal tissues and normal cells because of their low selectivity for cancer cells, so that, in the present situation, the use of such drugs is strictly restricted due to their side effects no matter how they are effective.

On the contrary, controlling methods of the expression of specific genes have recently been developed making use of nucleic acids and their derivatives. Since cancers are genetic diseases as described above, cancer cell-specific effects can fully be expected by such expression controlling methods when a specific gene, particularly a malignant transformation factor, is used as the target.

One of such means is antisense method. In this method, a short oligonucleotide (approximately 15 to 30 base length) having a nucleotide sequence complimentary to a nucleotide sequence of a gene to be used as a target is introduced into cells to effect inhibition of transcription or translation of the malignant transformation gene.

However, since single-stranded oligonucleotides to be used in the antisense method have low stability in cells and are quickly metabolized in the living body, they have not yet been realized as medicines.

On the other hand, expression of cell growth-related genes is naturally impelled in cancer cells due to their high cell division capacity. Because of this, these factors related to DNA synthesis and cell growth have been used as targets of anticancer agents. However, it is known that the degree of expression of each gene varies depending on each individual, organ and tissue type, and the degree varies greatly among cells even in the same cancer tissue. As the result, the conventional drugs in which a single cell growth factor is used as a target have limited efficacy due to narrow spectrum.

Accordingly, the object of the present invention is to provide an oligonucleotide or the derivative thereof useful as a pharmaceutical composition of an anticancer the like agent having broad spectrum and strong efficacy, as well as a method for preventing and treating cancers making use of the pharmaceutical composition.

DISCLOSURE OF THE INVENTION

In view of the above, the inventors of the present invention have firstly paid attention to a fact that an intracellular transcription factor E2F is possessed of excellent properties as a target of anticancer agents. The intracellular transcription factor E2F has been discovered as a factor which binds to the adenovirus E2 promoter, and its further studies have revealed that it takes an important role in the control of cell growth (Nevis, J. R., Science, 258, 424–429 (1992); International Publication WO 95/11687). That is, it has been revealed that E2F binds to specific sequences each consisting of 8 bases (TTTCGCGC and TTTCCCGC) which exist in the promoter region of DNA polymerase α, dehydrofolate reductase and c-myc genes that are essential for DNA synthesis and cell growth, thereby activating transcription of these genes.

In consequence, the present inventors have assumed that expression of cell growth-related genes could be inhibited altogether by inhibiting the function of E2F protein and that the result would render possible development of a novel anticancer agent having broad spectrum and strong efficacy.

However, it has been reported that the E2F protein is not a single protein but consists of at least 5 different proteins which form a so-called gene family (see for example, Huber, H. E. et al., Proc. Natl. Acad. Sci., USA, 90, 3525–3529 (1993) and Lees, J. A. et al., Mol. Cell. Biol., 13, 7813–7825 (1993)). In addition, functional allotment of each E2F protein is not yet clear. Under such conditions, it has been difficult to inhibit expression of all E2F genes even by the use of the usual antisense method.

As a consequence, the present inventors have accomplished the present invention based on a finding that exhaustion of intracellular E2F proteins can be induced by absorbing the intracellular E2F proteins with a double-stranded oligonucleotide containing TTTSSCGS which is a recognition sequence of these E2F proteins, so that expression of E2F-concerning cell growth-related genes can be inhibited and markedly strong cancer cytotoxic activity can be obtained.

Accordingly, the present invention comprises the following constructions.

1. A double-stranded oligonucleotide or a derivative thereof which comprises 15 to 40 base pairs, wherein at least one side of the strands contains at least one nucleotide sequence represented by 5'-TTTSSCGS-3', in which S represents G or C.
2. The double-stranded oligonucleotide or a derivative thereof according to the above item 1, wherein the base pairs are 15 to 32.
3. The double-stranded oligonucleotide or a derivative thereof according to the above item 1, wherein the base pairs have 1 to 5 of a nucleotide sequence represented by 5'-TTTSSCGS-3' on one side of the strands.
4. The double-stranded oligonucleotide or a derivative thereof according to the above item 1, wherein the base pairs have a nucleotide sequence represented by 5'-(TTTSSCGS)$_n$-3', in which n is 2 to 5, on one side of the strands.
5. The double-stranded oligonucleotide or a derivative thereof according to the above item 4, wherein n is 2 to 4.
6. The double-stranded oligonucleotide or a derivative thereof according to the above item 1 or 4, which has a nucleotide sequence shown in Sequence ID No. 1.
7. The double-stranded oligonucleotide or a derivative thereof according to the above item 1, wherein the base pairs have a nucleotide sequence represented by 5'-TTTSSCGSSAAA-3' (SEQ ID NO:9) on one side of the strands.

8. The double-stranded oligonucleotide or a derivative thereof according to the above item 1 or 7, which has a nucleotide sequence shown in Sequence ID No. 2.

9. The double-stranded oligonucleotide or a derivative thereof according to the above item 1, wherein the base pairs have a nucleotide sequence represented by 5'-SCGSSAAATTTSSCGS-3' (SEQ ID NO:10) on one side of the strands.

10. The double-stranded oligonucleotide or a derivative thereof according to the above item 1 or 9, which has a nucleotide sequence shown in Sequence ID No. 3.

11. The double-stranded oligonucleotide or a derivative thereof according to the above item 1, which is in a dumbbell form.

12. The double-stranded oligonucleotide or a derivative thereof according to the above item 11, wherein G and C of the 1-position base pair of Sequence ID No. 3 are linked together via TTTTT and C and G of the 28-position base pair of the same are linked together via TTTTT.

13. A pharmaceutical composition which comprises as an active ingredient at least one of the oligonucleotides or derivatives thereof described in the above items 1 to 12.

14. The pharmaceutical composition according to the above item 13, which is a preventive and therapeutic agent of cancers.

15. A method for preventing and treating cancers which comprises administering a therapeutically effective amount of the pharmaceutical composition of the above item 14 to animals including human.

The double-stranded oligonucleotide of the present invention comprises 15 to 40 base pairs, which contains at least one nucleotide sequence represented by 5'-TTTSSCGS-3' (S represents G or C) on at least one side of the strands (the sequence 5'-TTTSSCGS-3' is called basic sequence hereinafter). For example, a double-stranded oligonucleotide having one basic sequence means that one of the double strands forms a sequence 5'-N . . . . . NTTTSSCGSN . . . . . N-3' (SEQ ID NO:11) (N is A, T, G or C) through the linkage of a total of 7 to 32 optional base N to its 5'-end and/or 3'-end and the other strand is a sequence complementary to the former sequence, and the double-stranded oligonucleotide may be either in linear or circular form.

Also, when the basic sequence is present in plural numbers, the oligonucleotide sequence can be formed in the same manner as the above case of one basic sequence, by replacing a partial or entire portion of the aforementioned sequence N . . . . . N with the basic sequence. The replacement of basic sequence may be effected by continuously linking the base sequence via or not via a single or a plurality of N or in a combination thereof. Also, the S bases in each basic sequence may be the same or different from one another.

The double-stranded oligonucleotide of the present invention may have preferably 15 to 32 base pairs, more preferably 22 to 32 base pairs.

When the double-stranded oligonucleotide of the present invention is constructed solely with the basic sequence, the number of the basic sequence may be preferably 2 to 5, more preferably 2 to 4, per one strand. The term "constructed solely with the basic sequence" means a double-stranded oligonucleotide represented by 5'-(TTTSSCGS)$_n$-3' wherein n is preferably 2 to 5, more preferably 2 to 4. Particularly preferred is the sequence of the Sequence ID No. 1.

When the double-stranded oligonucleotide of the present invention is constructed by including N, preferred is a case in which the basic sequence is arranged on both strands, more preferred is a case in which both strands own all or a part of SSCGS jointly or a case in which 5'-TTTSSCGS-3' and its complementary base pair 5'-SCGSSAAA-3' are continued base pairs, and most preferred is a case in which a nucleotide sequence represented by 5'-TTTSSCGSSAAA-3' (SEQ ID NO:9) or a nucleotide sequence represented by 5'-SCGSSAAATTTSSCGS-3' (SEQ ID NO:10) is arranged on one side of the strands. Illustrative examples are those respectively disclosed in Sequence ID Nos. 2 and 3, though not particularly limited thereto.

The oligonucleotide of the present invention can generally be synthesized using a commercially available DNA synthesizing apparatus in accordance with the known techniques. In that case, phosphodiester linkage may be replaced by methyl phosphate linkage (U.S. Pat. No. 4,511,713) or phosphorothioate linkage (JP-A-1-503302; the term "JP-A" as used herein means an "unexamined published Japanese patent application") in view of intracellular incorporation and stability. Each of these types can also be synthesized using a commercially available DNA synthesizing apparatus. Formation of a double-stranded oligonucleotide after the synthesis may be effected by usually used annealing techniques.

In addition, it is possible to increase intracellular incorporation by binding cholesterol or the like fat-soluble compound to the 5'- or 3'-end of oligonucleotide containing such sequence or to obtain markedly high nuclease resistance by forming the double-strand into so-called dumbbell type DNA through bonding of its both terminals using an enzyme or the like (Clusel, C. et al., *Nucleic Acids Res.*, 21, 3405–3411 (1993)).

According to the dumbbell-shaped double-stranded oligonucleotide of the present invention, a nucleotide sequence which does not form hydrogen bonding is linked to both terminals of the double-stranded oligonucleotide in such a manner that the double-stranded oligonucleotide forms a circular single-stranded oligonucleotide including the double-stranded portion. In other words, the aforementioned nucleotide sequence which does not form hydrogen bonding is linked to the 5'- and 3'-end bases of each terminal of the double-stranded oligonucleotide, thereby forming a dumbbell shape in which both terminals are single-stranded and the central portion is double-stranded. The nucleotide sequence which does not form hydrogen bonding may have a length of 1 to 15 bases, preferably 3 to 8 bases, per one terminal.

An example of such a type is the dumbbell type double-stranded oligonucleotide shown in the aforementioned item 12 in which G and C of the 1-position base pair of Sequence ID No. 3 are linked together via TTTTT, and C and G of the 28-position base pair of the same are linked together via TTTTT.

In this connection, N of the dumbbell moiety of the dumbbell type double-stranded oligonucleotide is not included in the bases of 15 to 40 base pairs which constitute the double-stranded oligonucleotide of the present invention.

In consequence, examples of the double-stranded oligonucleotide derivative of the present invention include those which have an effect to inhibit expression of E2F-concerning growth-related genes similar to the case of the aforementioned oligonucleotide, in which the phosphodiester linkage is replaced by methyl phosphate linkage or phosphorothioate linkage, a fat-soluble compound is linked to its 5'- or 3'-end, or it forms a dumbbell form double-stranded oligonucleotide.

Since the double-stranded oligonucleotide or a derivative thereof of the present invention (hereinafter, referred to as inventive compound) has strong effects to kill cells and inhibit expression of E2F-concerning growth-related genes, it can be used as an active ingredient of pharmaceutical compositions.

The pharmaceutical composition of the present invention can contain the inventive double-stranded oligonucleotides or derivatives thereof alone or as a combination thereof in the same composition, and blending ratio of each double-stranded oligonucleotide or a derivative thereof can be changed optionally.

The pharmaceutical composition of the present invention can be prepared from the aforementioned double-stranded oligonucleotide or a derivative thereof and a known pharmaceutical carrier and is particularly useful as an agent for the prevention and treatment of cancers.

When the double-stranded oligonucleotide of the present invention or a derivative thereof is applied as a medicine to mammals including human, it can be made into various dosage forms depending on each preventive or therapeutic purpose, such as injections, suppositories, preparations for external use (for example, cataplasmas, tapes and the like adhesive preparations, ointments, creams and lotions), eye drops, nasal drops and the like, and these preparations can be produced in accordance with respective medicine preparation techniques known to those skilled in the art.

When injections are produced, subcutaneous, intramuscular and intravenous injections can be prepared by mixing the inventive compound with a pH adjusting agent, a buffer agent, a stabilizing agent, an isotonic agent, a local anesthetic and the like in an ordinary method. Examples of the pH adjusting agent and buffer agent in this case include sodium citrate, sodium acetate, sodium phosphate and the like. As the stabilizing agent, sodium pyrosulfite, EDTA, thioglycolic acid, thiolactic acid and the like may be used. Examples of the local anesthetic include procaine hydrochloride, lidocaine hydrochloride and the like. Sodium chloride, glucose and the like may be used as the isotonic agent.

Suppositories can be produced by mixing the inventive compound with pharmaceutical carriers known in the art such as polyethylene glycol, lanolin, cacao butter and fatty acid triglyceride, as well as Tween (trade name) and the like surfactants as occasion demands, and then shaping the resulting mixture in an ordinary method.

Ointments are produced by blending the inventive compound with generally used base materials, stabilizers, moistening agents, lubricant and the like depending on each purpose, and mixing the formulation in an ordinary method. Examples of such base materials include liquid paraffin, white petrolatum, bleached beeswax, octyldodecyl alcohol, paraffin and the like. Examples of the preservatives include methyl paraoxybenzoate, ethyl paraoxybenzoate, propyl paraoxybenzoate and the like.

Adhesive preparations are produced in the usual way by coating a generally used support with the aforementioned ointments, creams, gels, pastes or the like. Examples of suitable support include woven or non-woven fabric made of cotton, staple fiber, chemical fiber and the like, and films or foam sheets of soft vinyl chloride, polyethylene, polyurethane and the like.

In addition, the compound of the present invention may be administered by encapsulating it into liposomes, in which the active ingredient is dispersed in fine particles composed of aqueous concentric layers adherent to fatty layers or used as a pharmacological composition to be included in other forms. Depending on its solubility, the effective compound may be present in both aqueous and fatty layers or used in the form of so-called liposome suspension. The hydrophobic layer consists of a phospholipid such as lecithin, a steroid such as cholesterol, a slightly ionic surfactant such as dicetyl phosphate, stearyl amine or phosphatidic acid, and/or other hydrophobic compounds. Particle size of liposomes is generally within the range of from about 15 nm to about 5 microns.

Though the content of the oligonucleotide of the present invention in pharmaceutical preparations varies depending on each preparation, it may preferably be within the range of approximately from 1 to 70% by weight in general.

Administration method of the pharmaceutical preparation of the present invention is not particularly limited and can be optionally decided depending on each dosage form, age, sex and other conditions of each patient, degree of symptoms and the like. For example, an injection preparation may be used for intravenous injection as such or by mixing it with usual auxiliary solutions such as of glucose, amino acids and the like, or it may be used alone for intraarterial, intramuscular, subcutaneous or intraperitoneal injection as occasion demands. Suppositories are administered into the rectum and ointments are applied to the skin, oral mucosa and the like.

Dose of the compound of the present invention can be optionally selected depending on each administration method, age, sex and other conditions of each patient, degree of symptoms and the like. In general, the compound of the present invention may be administered in an approximate dose of from 0.01 to 1,000 mg/kg/day, preferably from 0.01 to 10 mg/kg/day. The daily dose recited above may be used once a day or divided into 2 to 4 daily doses.

BEST MODE OF CARRYING OUT THE INVENTION

The present invention is now illustrated in greater detail with reference to the following Inventive, Test and Formulation Examples, but it should be understood that the present invention is not deemed to be limited thereto.

INVENTIVE EXAMPLE 1

Design and Production of Double-stranded Oligonucleotide

Using a commercially available automatic DNA synthesizer (manufactured by Applied Biosystems) in which a β-cyanoethyl synthesis method was employed, oligonucleotides represented by Sequence ID Nos. 1 to 3 and their respective complementary chains were synthesized, and each pair of the oligonucleotides was mixed and double-stranded (linear chain) by an ordinary annealing technique. Also, the dumbbell type double-stranded oligonucleotide (hereinafter, referred simply to as "dumbbell type"), in which G and C of the 1-position base pair of Sequence ID No. 3 were linked together via TTTTT and C and G of the 28-position base pair of the same were linked together via TTTTT, was prepared by synthesizing a 38 mer single-stranded DNA fragment using the 20-position C as the 5'-end, effecting formation of the same double-stranded moiety of Sequence ID No. 3 in the molecule by annealing reaction and then rounding the product with T4 ligase.

Figure 1:
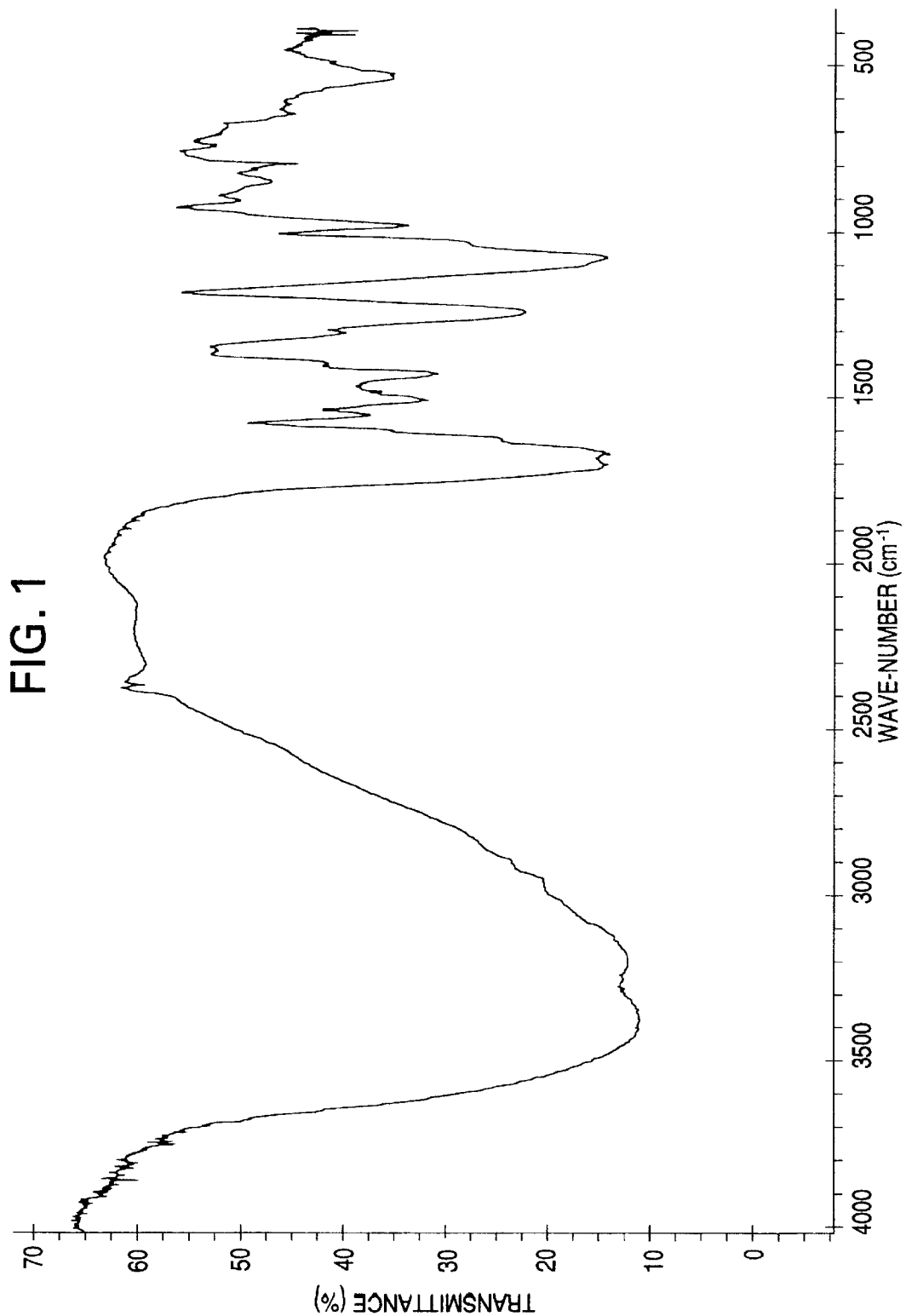
FIG. 1 is a graph showing infrared absorption spectrum of the oligonucleotide represented by Sequence ID No. 1.

A chart of infrared absorption spectrum (KBr method) of Sequence ID No. 1 is shown in FIG. 1.

Figure 2:
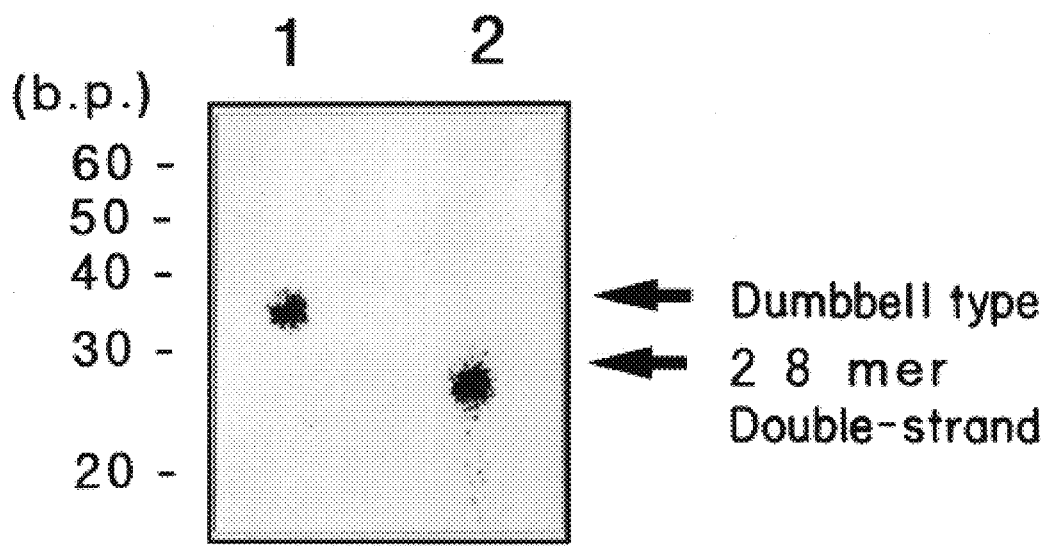
FIG. 2 is a graph showing results of a test carried out using a digestion enzyme specific for single-stranded DNA to confirm production of a dumbbell type double-stranded oligonucleotide.

Also, properly formed structure of the thus produced dumbbell type was confirmed by a digestion test using a digestion enzyme specific for single-stranded DNA, with the results shown in FIG. 2. That is, the dumbbell type oligonucleotide labeled with $^{32}P$ was digested with a single-stranded DNA-specific digestion enzyme, mung bean nuclease, subjected to 20% polyacrylamide gel electrophoresis, and then the resulting gel was dried to analyze its readioactivity distribution using BAS-2000 Bio-Imaging Analyzer (manufactured by Fuji Photo Film). As the result, judgement of the mobility of each detected band confirmed that the molecule, which has been subjected to the ring closure reaction, lost the single-stranded TTTTT moiety by the mung bean nuclease digestion to form the same 28 mer length double-stranded oligonucleotide of Sequence ID No. 3 having a dumbbell type structure.

TEST EXAMPLE 1

Cytotoxic activities of the double-stranded oligonucleotide obtained in Inventive Example 1, other oligonucleotides shown in Table 1 synthesized in the same manner and adriamycin were examined using human cervical carcinoma HeLa cells in a cultured system. That is, $5 \times 10^2$ cells/100 $\mu$l/well of HeLa cells suspended in 10% fetal bovine serum-supplemented MEM medium were seeded in a 96 well culture dish, and, after 2 days of culturing, each well was charged with 100 $\mu$l of MEM medium containing 4 $\mu$M of lipofectin and each oligonucleotide which have been allowed in advance to react with each other at room temperature for 1 hour. After additional 3 days of culturing, the number of cells was determined by Crystal Violet method to calculate $IC_{50}$ value. The results are shown in Table 1.

TABLE 1

| Compounds | $IC_{50}$ ($\mu$M) | Remarks |
| --- | --- | --- |
| Sequence ID No. 1 | 3 | Inventive compounds |
| Sequence ID No. 2 | 0.4 | " |
| Sequence ID No. 3 | 2 | " |
| Dumbbell type | 10 | " |
| Sequence ID No. 4 | 40 | Comparative compounds |
| Sequence ID No. 5 | 260 | " |
| Sequence ID No. 6 | >667 | " |
| Sequence ID No. 7 | 30 | " |
| Sequence ID No. 8 | >667 | " |
| Adriamycin | 250 | " |

As is evident from the results shown in Table 1, the inventive compounds of Sequence ID Nos. 1 to 3 and dumbbell type have several times to 1,000 times or more stronger cytotoxic activity than that of the comparative compounds of Sequence ID Nos. 4 to 8. In this connection, Sequence ID No. 4 is a sequence prepared by shuffling the nucleotide sequence of Sequence ID No. 1. Sequence ID No. 5 is antisense of E2F-1 (one of the E2F proteins) and Sequence ID No. 7 is antisence of c-myc, and Sequence ID No. 6 is nonsense of E2F-1 and Sequence ID No. 8 is nonsense of c-myc.

TEST EXAMPLE 2

In order to confirm that the cytotoxic activity of the compounds of the present invention shown in Test Example 1 is caused by the inhibition of E2F function, changes in the amount of expression of E2F-1 itself and c-myc, c-myb and cyclin D1 considered to be regulated by E2F-1 were examined by Western blotting. That is, HeLa cells were cultured for 2 days in a 24 well plate and then treated with each oligonucleotide for 16 hours in the same manner as described in Test Example 1. Thereafter, the resulting cells were treated with a solubilizing agent (50 mM Tris buffer pH 7.5/0.05% SDS) to obtain a crude cell extract. After determination of protein concentration in each sample, a predetermined amount of the protein extract was subjected to SDS-PAGE electrophoresis. After the electrophoresis, protein was transferred onto a nitrocellulose membrane to determine the amount of expressed protein in each sample using respective monoclonal antibodies shown in Table 2. As a control test, Western blotting was carried out in the same manner using GAPDH (glutaraldehyde phosphate dehydrogenase) which hardly changes by the condition of cell growth. Table 2 shows the action of inventive and comparative compounds upon the expression of E2F-1 and E2F-related proteins.

TABLE 2

| | Oligonucleotide | | | |
| --- | --- | --- | --- | --- |
| Protein types | Sequence ID No. 5 (0.5 $\mu$M)* | Sequence ID No. 6 (0.5 $\mu$M)* | Sequence ID No. 1 (0.01 $\mu$M)* | Sequence ID No. 4 (0.01 $\mu$M)* |
| E2F-1 | A | B | B | B |
| c-myc | A | B | A | B |
| c-myb | A | B | A | B |
| cyclin D1 | B | B | B | B |
| GAPDH | B | B | B | B |

Remarks:
"*":an amount of oligonycleotide used.
A: inhibition of expression
B: no change in expression
Sequence ID No. 1 is inventive compound.
Sequence ID Nos. 4, 5 and 6 are comparative compounds.

Figure 3:
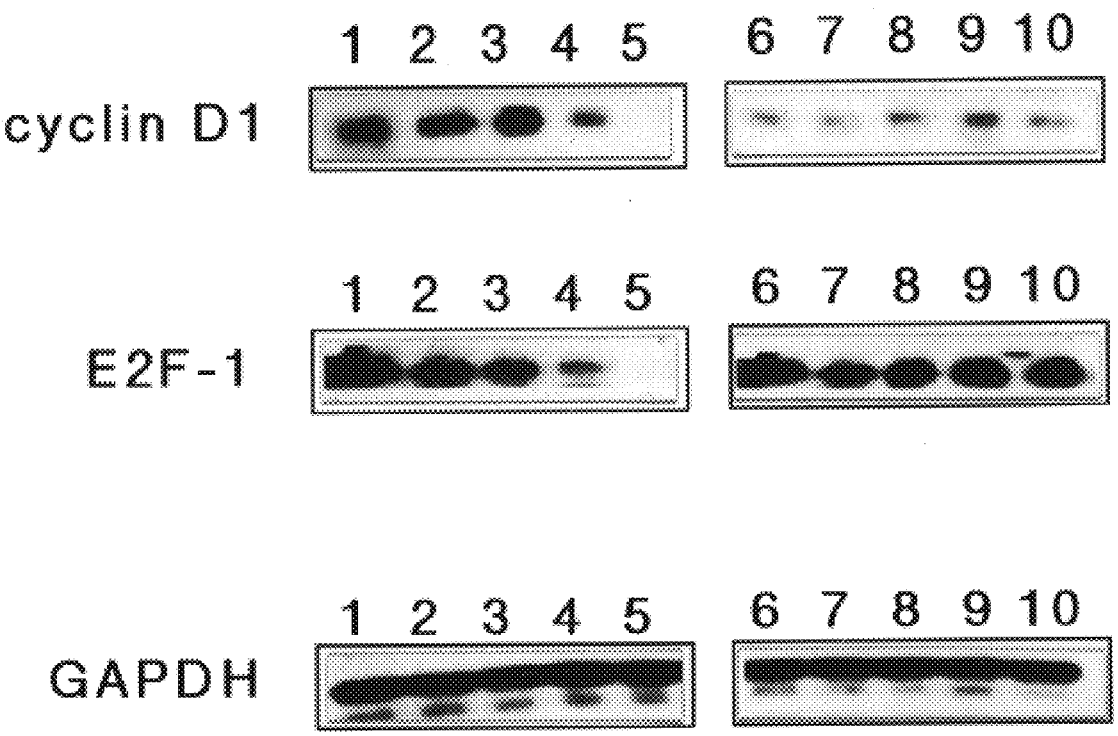
FIG. 3 is a graph showing results of a western blot analysis of E2F-regulated gene proteins after treatment with the inventive compound (dumbbell type, Sequence ID No. 1).

As the results, expression of c-myc and c-myb regulated by E2F-1 was inhibited in a specific manner by the treatment with 0.01 $\mu$M of the inventive compound of Sequence ID No. 1. In this case, changes in the expression of E2F-1 protein and GAPDH were not detectable. In the case of the double-stranded oligonucleotide of Sequence ID No. 4 in which the E2F binding sequence was deleted by rearranging the sequence of Sequence ID No. 1, it did not change expression of the gene products, namely proteins, measured this time. In addition, as shown in FIG. 3, the results of examination carried out after 48 hours of the oligonucleotide treatment confirmed that the dumbbell type compound having improved stability reduced the amount of proteins of cyclin D1 and E2F-1 on which the compound of Sequence ID No. 1 did not act. In this case, changes in the protein expression of GAPDH were not detectable.

Results of an examination on the effect of an antisense oligonucleotide (Sequence ID No. 5) on E2F-1 carried out at the same time revealed that, unlike the case of the inventive compound, it can induce inhibition of the expression of E2F-1-regulated genes through inhibition of the transcription of E2F-1. However, the compound of Sequence ID No. 5 required 50 times higher concentration than that of the inventive compound for exerting similar degree of the inhibition effect of the inventive compound.

TEST EXAMPLE 3

In order to confirm that the reduction of the E2F-regulated protein found in Test Example 2 is caused by the inhibition of gene expression via reduced mRNA synthesis, changes in the amount of mRNA after treatment with each of the Sequence ID No. 1 and dumbbell type compounds of the present invention were examined. Namely, HeLa cells were treated with each of the inventive Sequence ID No. 1, dumbbell type compounds and 4 μM of lipofectin for 48 hours in the same manner as described in Test Example 2, and the amount of each type of mRNA in cells was analyzed by RT-PCR (reverse transcription-polymerase chain reaction) method. That is, RNA in the cells was purified using RNeasy RNA Purification Kit (manufactured by Qiagen), and cDNA was prepared using the thus purified RNA as a template and poly(dT)$_{12-18}$ as a primer, with the aid of AMW reverse transcriptase and First Strand Synthesis Kit (manufactured by Life Science). Thereafter, in order to effect PCR amplification of mRNA of each gene regulated by E2F, corresponding cDNA fragment was amplified by the PCR method using corresponding primer set. In this case, GAPDH mRNA which hardly changes under the cell growth conditions was simultaneously used as an internal standard. The number of times of the repetition of amplification for each run was set within such a range that linear amplification could be obtained. Each of the thus PCR-amplified samples was subjected to 2% agarose gel electrophoresis, DNA in the resulting gel was stained with ethidium bromide and then UV rays were applied to the gel to visualize the DNA. Such a procedure renders possible judgement of the amount of DNA as the fluorescence intensity of each DNA band (Wang, H. et al., *Anal. Biochemistry*, 223, 251–258, 1994).

Figure 4:
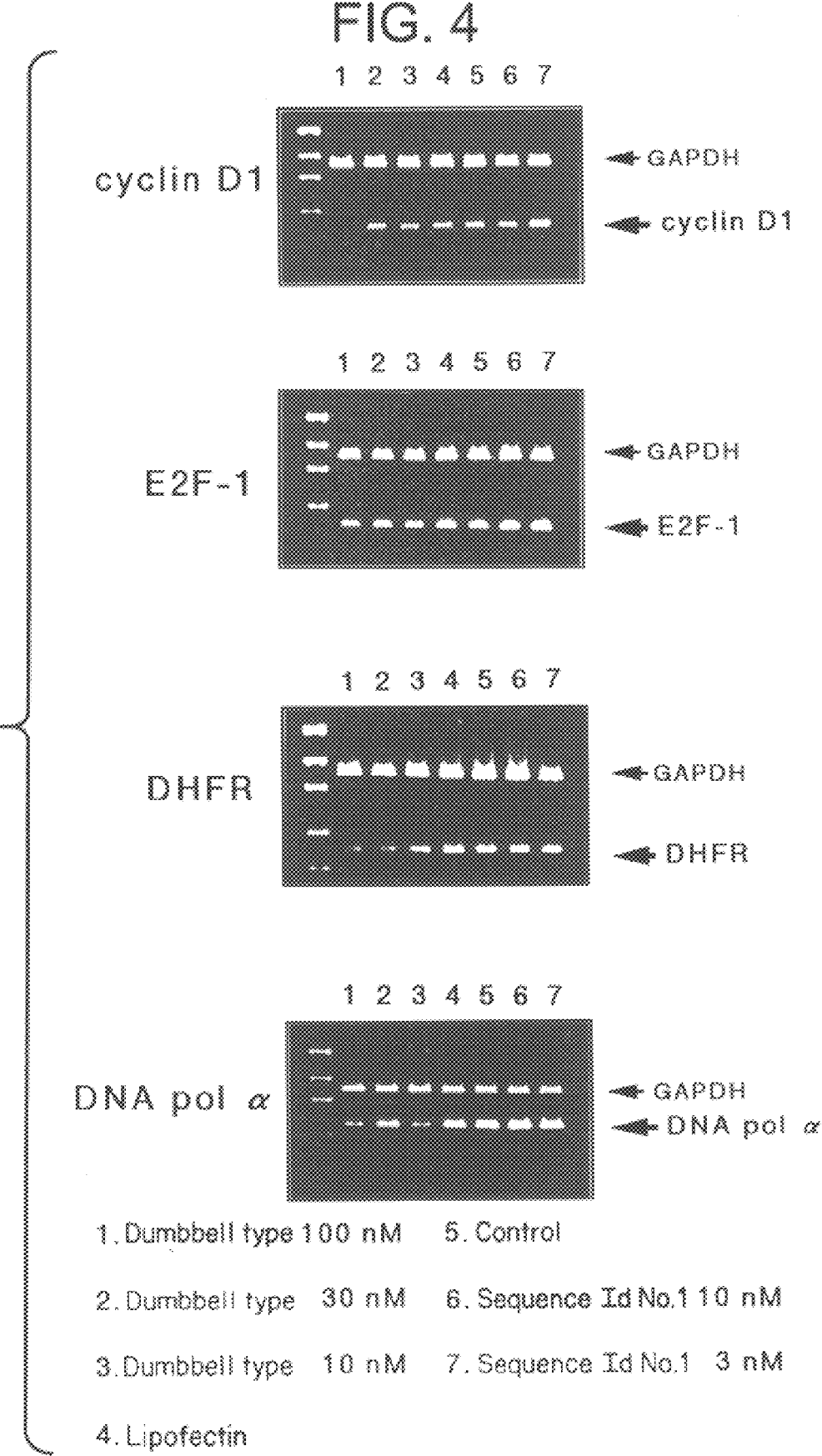
FIG. 4 is a graph showing results of an RT-PCR analysis of the amount of mRNA changed by the inventive compound.

Results of the agarose electrophoresis are shown in FIG. 4 (the amount of DNA was judged as described above). The simultaneously amplified GAPDH mRNA did not change by the oligonucleotide treatment, but the mRNA level of cyclin D1, whose expression is regulated by E2F, and of E2F-1 itself decreased when treated with the dumbbell type compound. In addition to this, the dumbbell type compound also induced reduction of the mRNA level of other E2F-regulated genes of DHFR and DNA polymerase α (DNA pol α).

TEST EXAMPLE 4

Figure 5:
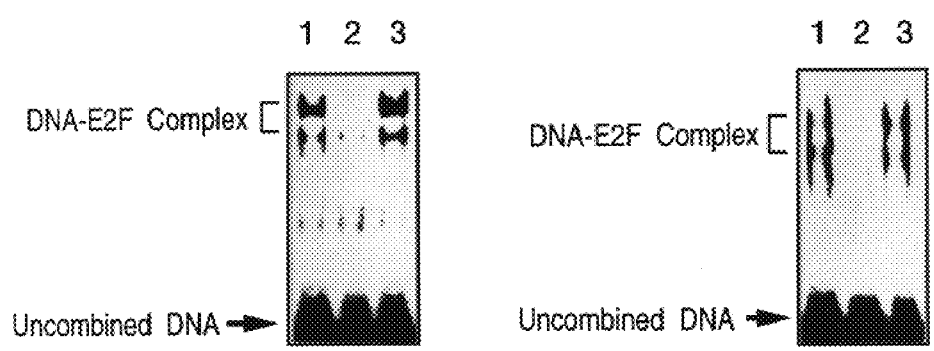
FIG. 5 is a graph showing results of a gel shift assay carried out to analyze binding of E2F protein to the inventive compound.

In order to confirm that such an inhibition of gene expression via reduced expression quantity of mRNA is based on the sequence-specific competitive inhibition of double-stranded oligonucleotide with E2F protein for its transcription region, binding ability of E2F protein to double-stranded oligonucleotide was examined by a gel shift assay shown in FIG. 5. That is, each of the compounds of Sequence ID Nos. 1 and 3 and dumbbell type was labeled with $^{32}$P using [γ-$^{32}$P] ATP and T4 polynucleotide kinase. This was mixed with a cell extract which has been prepared in accordance with the method of Dignam, J. D. et al. (*Nucl. Acids Res.*, 11, 1475–1489, 1983), and the resulting mixture was subjected to 20 minutes of reaction at 4° C. and then to 4% acrylamide gel electrophoresis. After the electrophoresis, the resulting gel was dried to analyze using BAS-2000 Bio-Imaging Analyzer (manufactured by Fuji Photo Film).

As the result, a protein-bound double-stranded oligonucleotide appeared as a band (control) with a slower mobility than the double-stranded oligonucleotide itself. This protein-DNA complex disappeared when a double-stranded oligonucleotide having the same sequence with no $^{32}$P labeling (non-labeled Sequence ID No. 1 or 3) was added in a 100 times larger amount than that of the $^{32}$P-labeled compound, but did not disappear by the addition of 100 times larger amount of a double-stranded oligonucleotide in which the E2F protein binding sequence has been shuffled (Sequence ID No. 4), so that this complex can be concluded as a complex of a protein which binds to the E2F protein binding sequence in a specific fashion, namely the E2F protein, and the double-stranded oligonucleotide.

On the basis of the above results, it can be considered that the compound of the present invention induces inhibition of the expression of growth-related genes which are regulated by E2F, through its function to undergo sequence-specific competitive inhibition of the binding of E2F protein to the transcription region at a low concentration, thereby exerting its effect to inhibit growth of cancer cells which is stronger than that of the antisense oligonucleotide.

PREPARATION EXAMPLE 1

Injection Preparation

| | |
|---|---|
| Inventive compound | 5 mg |
| Distilled water for injection use | balance |
| per ampoule | 5 ml |

An injection preparation was prepared in an ordinary method using the above formulation.

PREPARATION EXAMPLE 2

Suppository Preparation

| | |
|---|---|
| Inventive compound | 20 mg |
| Witepsol W-35 (trade name, manufactured by Dynamite Novel) | 1,380 mg |
| per one | 1,400 mg |

A suppository preparation was prepared in an ordinary method using the above formulation.

Industrial Applicability

Since the double-stranded oligonucleotide of the present invention or a derivative thereof can inhibit expression of growth-related genes which are regulated by E2F, through its function to undergo sequence-specific competitive inhibition of the binding of E2F protein to the transcription region at a low concentration, it can inhibit growth of tumors and therefore is useful as an agent having low side effects for use in the prevention and treatment of cancers.

What is claim is:

1. An isolated double-stranded oligonucleotide which binds to E2F transcription factor protein and consists of 15–40 base pairs, wherein at least one strand of said double-stranded oligonucleotide contains at least one nucleotide sequence represented by 5'-TTTSSCGSSAAA-3' (SEQ ID NO:9), wherein S represents G or C; wherein said double-stranded oligonucleotide has a phosphodiester backbone, a methyl phosphate backbone or a phosphorothioate backbone, and wherein, optionally, a fat-soluble compound is linked to the 5'- or 3'-end of said double-stranded oligonucleotide; and further wherein said double-stranded oligonucleotide forms a dumbbell form double-stranded oligonucleotide.

2. An isolated double-stranded oligonucleotide which binds to E2F transcription factor protein and consists of 15–40 base pairs, wherein at least one strand of said double-stranded oligonucleotide contains at least one nucleotide sequence represented by 5'-CGGCCACAATTTCGCGCCAAACTTGACCGC-3' (SEQ ID NO:2), wherein S represents G or C; wherein said double-stranded oligonucleotide has a phosphodiester backbone, a methyl phosphate backbone or a phosphorothioate backbone, and wherein, optionally, a fat-soluble compound is linked to the 5'- or 3'-end of said double-stranded oligonucleotide; and further wherein said double-stranded oligonucleotide forms a dumbbell form double-stranded oligonucleotide.

3. An isolated double-stranded oligonucleotide which binds to E2F transcription factor protein and consists of 15–40 base pairs, wherein at least one strand of said double-stranded oligonucleotide contains at least one nucleotide sequence represented by 5'-SCGSSAAATTTSSCGS-3' (SEQ ID NO:10), wherein S represents G or C; wherein said double-stranded oligonucleotide has a phosphodiester backbone, a methyl phosphate backbone or a phosphorothioate backbone, and wherein, optionally, a fat-soluble compound is linked to the 5'- or 3'-end of said double-stranded oligonucleotide; and further wherein said double-stranded oligonucleotide forms a dumbbell form double-stranded oligonucleotide.

4. An isolated double-stranded oligonucleotide which binds to E2F transcription factor protein and consists of 15–40 base pairs, wherein at least one strand of said double-stranded oligonucleotide contains at least one nucleotide sequence represented by 5'-GCTTTCCCGCCAAATTTCGCGCGAAAGC-3' (SEQ ID NO:3), wherein S represents G or C; wherein said double-stranded oligonucleotide has a phosphodiester backbone, a methyl phosphate backbone or a phosphorothioate backbone, and wherein, optionally, a fat-soluble compound is linked to the 5'- or 3'-end of said double-stranded oligonucleotide; and further wherein said double-stranded oligonucleotide forms a dumbbell form double-stranded oligonucleotide.

5. The isolated double-stranded oligonucleotide as claimed in claim 4, wherein the G:C base pair at position 1 of SEQ ID NO:3 is linked to the C:G base pair at position 28 of SEQ ID NO:3 via TTTTT.

* * * * *